United States Patent
Mah

(10) Patent No.: US 11,771,732 B2
(45) Date of Patent: Oct. 3, 2023

(54) DERMAGRANT COMPOSITION

(71) Applicant: DuraScience Inc., New York, NY (US)

(72) Inventor: James Nitit Mah, New York, NY (US)

( * ) Notice: Subject to any disclaimer, the term of this patent is extended or adjusted under 35 U.S.C. 154(b) by 0 days.

(21) Appl. No.: 16/679,275

(22) Filed: Nov. 10, 2019

(65) Prior Publication Data

US 2020/0069763 A1   Mar. 5, 2020

(51) Int. Cl.
| | | |
|---|---|---|
| *A61K 36/00* | (2006.01) | |
| *A61K 38/05* | (2006.01) | |
| *A61K 35/60* | (2006.01) | |
| *A61K 36/899* | (2006.01) | |
| *A23L 33/105* | (2016.01) | |
| *A23L 33/18* | (2016.01) | |
| *A61K 36/73* | (2006.01) | |

(52) U.S. Cl.
CPC ............ *A61K 38/05* (2013.01); *A23L 33/105* (2016.08); *A23L 33/18* (2016.08); *A61K 35/60* (2013.01); *A61K 36/73* (2013.01); *A61K 36/899* (2013.01); *A23V 2002/00* (2013.01)

(58) Field of Classification Search
None
See application file for complete search history.

(56) References Cited

U.S. PATENT DOCUMENTS 9,931,364 B2 *   4/2018   Mager .................... A23L 33/40

\* cited by examiner

*Primary Examiner* — Russell G Fiebig
(74) *Attorney, Agent, or Firm* — Bullock Law; Stephen Bullock

(57) ABSTRACT

In an embodiment, a nutritional supplement composition is provided. The nutritional supplement composition is provided including a fish extract derived from fish collagen dipeptide, corn powder from from the *Zea mays* l. strain and raspberry extract of the *Rubus idaeus* strain. The nutritional supplement is in the form of a compound known as DERMAGRANT™.

1 Claim, No Drawings

DERMAGRANT COMPOSITION

BACKGROUND

In the past, we commonly used all parts of natural foods when we consumed a meal. Human eating patterns naturally accessed nutrients available from what was eaten and very little nutrients were wasted as a result. For example, when eating fish, the muscular parts of the fish were consumed along with other parts such as connective tissue. When eating plants, the edible portion of the plant was consumed in its entirety. Our bodies would then filter out what was not consumable, such as the outer shell of a kernel of corn for example. As this occurred, our bodies would extract what nutrients could be found in the food to sustain and grow the human form. This allowed use of local foods to provide nutrients which were available, but was somewhat limited in that foods not available locally could not be used in most cases. Over time, we learned to travel and to ship food from where it was produced to where it could be consumed. Additionally, we learned to prepare foods, removing portions of the food which were either inedible, or undesirable. Removing the inedible parts typically provided some benefit, while parts that were simply undesirable sometimes held valuable ingredients.

Fish are typically available in most parts of the world, and can be consumed by those who choose to eat them. However, the collagen portions of fish are often removed in the preparation process. Collagen provides many useful raw materials for human bodies, related to connective tissue, for example. Therefore, finding a source of fish collagen can be potentially useful.

The *Zea mays* strain of maize is believed to originate in Central or South America, and is now generally available in many parts of the world. However, in prepared form it often loses some of the available nutrients of the original plant form. Thus, it would be potentially useful to provide a source of such material which the body can then extract nutrients from.

*Rubus idaeus* originates as the raspberry strain in parts of Europe. It contrasts from other strains such as *Rubus crataegifolius* found in Korea or *Rubus strigosus* found in north america. As a strain which is not available in all parts of the world, it offers some unique properties.

SUMMARY OF THE INVENTION

A nutritional supplement composition is provided including a fish extract derived from fish collagen dipeptide, corn powder from from the *Zea mays* l. strain and raspberry extract of the *Rubus idaeus* strain. The nutritional supplement is in the form of a compound known as DERMAGRANT™.

The foregoing, and other features and advantages of various embodiments of the invention, will be apparent from the following, more particular description of the embodiments of the invention, any accompanying drawings, and the claims.

DETAILED DESCRIPTION

A composition is provided as DERMAGRANT™. The specific embodiments described in this document represent exemplary instances of the present invention, and are illustrative in nature rather than restrictive.

In the following description, for purposes of explanation, numerous specific details are set forth in order to provide a thorough understanding of the invention. It will be apparent, however, to one skilled in the art that the invention can be practiced without these specific details. In other instances, structures and devices are shown in block diagram form in order to avoid obscuring the invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments.

The composition (referred to as DERMAGRANT™) is preferably formed of (1) a fish extract derived from fish collagen dipeptide, (2) corn powder from from the *Zea mays* l. strain and (3) raspberry extract of the *Rubus idaeus* strain.

The composition involves taking nutrients from fish collagen dipeptide, extracting this portion of the fish that is typically not used in fillets sold to consumers, for example. This nutrient is rich in amino acid, and peptides common to collagen, which have small particles and thus can be easily absorbed into the body and used instantly. Since the collagen is typically not available to consumers in many other circumstances, this provides nutrients potentially vital to rebuilding of collagen and associated connective tissue in the human body. For example, collagen typically provides building blocks of connective tissue in joints, such as cartilage vital to smooth functioning of knee, elbow and other joints, along with ligaments and tendons which bind bone-to-bone or bone-to-muscle.

The composition further involves obtaining nutrients from corn powder extracted from the *Zea mays* l. corn strain. This strain is known for capturing carbon molecules at a particularly high rate, providing for increased presence of one of the four most common elements of the human body. Additionally, by forming corn powder, we can capture all of the available nutrients of the *Zea mays* strain, potentially making available material from otherwise undigestible portions of corn, such as the epithelial outer covering of the kernels of the corn.

The composition also involves retrieving nutrients from raspberry extract of the *Rubus idaeus* strain. The *Rubus idaeus* strain originating in Europe and Northern Asia. Among other nutrients, Vitamin C and phenolics are typically present in the *Rubus idaeus* strain. Additionally, smaller amounts of flavonols, ellagic acid and hydroxycinnamate typically present in the *Rubus idaeus* strain. Moreover, polyphenolic compounds from raspberry seeds are believed to have antioxidant effects in vitro, and the seed are often present in the material from which the extract is drawn.

Results from Use of DERMAGRANT™

The composition includes a combination of the three extracts subjected to mixing and binding processes to further link the material provided therein. Typically, the combination of the extracts provides for a mix of building blocks for general healing and injury repair. The combination further provides specific materials having potential to aid in healing of specific types of injuries, enhancement of structures common in the skin and other parts of the body, and contribution to various aspects of general nutrition.

Collagen tissues in the human body may form bone, tendon, cartilage and other more specific structures. Collagen is also abundant in corneas, blood vessels, stomach and intestines, intervertebral discs, and the dentin in teeth. In muscle tissue, it serves as a major component of the endomysium. Collagen often constitutes one to two percent of muscle tissue and typically accounts for six percent of the weight of strong, tendinous, muscles.

Wound and Injury Healing Activity

Material from the collagen potentially aids in wound healing in a variety of ways, as the collagen derived from the fish source can be used by the human body in healing muscle, bone, tendons and other more specific structures found throughout the body. Additionally, the supply of nutrients from the *Zea mays* corn powder provides for additional raw materials used in wound healing and related rebuilding activity. Also, the raspberry extract provides specific building blocks useful in a variety of rebuilding activity in the body, potentially providing missing ingredients useful for healing of specific infirmities beyond those addressed by collagen and material from corn powder.

The benefit of the composition includes restoring and enhancing cells. Our cells constantly deteriorate in daily life. If there is no support to restore the deterioration, cellular damage will affect the body functions. DERMAGRANT™ composition is a supplementary factor that can restore the cells to the body balance without drug and substance usage. When cells are restored, in the next process, DERMAGRANT™ composition may accordingly boost cell strength, equivalent to increasing the effectiveness and the number of cells, while maximizing physical and mental abilities After the cellular restoration and boosting the cell strength, the next challenge is the protection to maintain the long-lasting quality of the cells. DERMAGRANT™ dietary supplement may help to protect and delay the cellular deterioration. This will also result in improving the immune system, as the immune system no longer needs to activate against inflammation or other forms of deterioration. When the cell functions are systematically restored, boosted and protected, DERMAGRANT™ dietary supplement may directly enhance physical and mental capacity to go beyond limits at each age and to live life fully as the pace of life requires a strong response to maintain youth and vigor.

The health benefits of DERMAGRANT™ are also potentially of value to children, and help to develop the strength of new cells and protect cells from early deterioration. Both are beneficial to the development of body, intelligence, memory, and positive emotions. The physical results may include i) restore cells for normal growth in each stage, ii) recover from illness, iii) build muscle, v) boost the immune system, vi) reduce the risk of the incidence of disease, vii) promote growth to maximum effectiveness, viii) adjust height, ix) improve body growth, x) efficient immunity and xi) increase energy. The wound and injury healing properties are potentially of particular assistance to children, as the nutrients provided assist specifically with structures often injured in sports or other childhood activities.

The composition also helps to restore the old damaged cells, repair damaged body tissues, delay the cellular deterioration, inhibit free radicals, and help the process of skin cell renewal in adults for glowing skin and younger appearance. Providing building blocks as previously mentioned contribute to enhancing balance, reducing exhaustion from stress and demands of healing, improving concentration and work efficiency, reducing healing time and longer term pain, and boosting the immune system to stay healthy Physical results may also include: a radiant and vibrant skin, younger appearance; reducing fatigue at work; restoring the reproductive system; refreshing the body; boosting the immune system; protecting against free radical formation; and preventing premature aging.

The compounds are typically dried and ground or milled to small particles, and subsequently combined in the desired ratio. The combination may remain as a powder to be added to food or pressed in a tablet. Alternatively, the compounds may be mixed in an aqueous or other liquid solution and thereby provided in liquid form.

In an embodiment, a preferred dosage, the total compound blended is 10.91 g, pressed into a single, large tablet. The compound may be sold under the DERMAGRANT™ name. The dosage may include a combination of 10.0 g of fish collagen dipeptide, 1.81 g of corn powder of the *Zea mays* l. extract, and 0.10 g of the *Rubus idaeus* raspberry extract. However, other ratios of the ingredients may be provided, and smaller or larger dosages may be used for particular applications.

Study of DERMAGRANT™ Effectiveness

A study of users of a trial formulation was conducted. The study focused initially on dermatological factors, but also considered other possible results. Results were broken down into dermatological factors and other potentially related factors. Participants reported the following results:

Eighty percent (80%) of participants reported reduced wrinkles and dermal creases, with a typical response of a seventy percent (70%) shallower dermal crease as a measured result.

Ninety percent (90%) of participants reported decreased skin blemishes.

Ninety-four percent (94%) of participants reported reduced inflammation. The participants reported skin inflammation decreasing to one tenth of incidence prior to use of DERMAGRANT™.

Eighty-six percent (86%) of participants reported an average ninety-five percent (95%) better pH balance of skin.

Ninety percent (90%) of participants reported an approximately ninety percent (90%) reduction in incidence of dermatitis.

Ninety-six percent (96%) of participants reported softer skin measured at a change of one hundred twenty percent (120%), which typically seemed to relate to better moisturizing of skin.

Eighty-six percent (86%) of participants reported an increase in firmness of skin of one hundred fifty percent (150%), which seemed to result from increased firmness of skin through rejuvenation of the extracellular matrix of the skin.

Eighty-three percent (83%) of participants reported approximately thirty percent (30%) lightening in skin shade, which may be related to the results associated with blemishes, inflammation and moisturizing.

Additional results beyond those specific to skin layers and skin cells were also observed.

Eighty-seven percent (87%) of participants were found to have a ninety percent (90%) improvement in gut microbacterial balance of the stomach and intestines, and this appeared to relate to and help reduce skin inflammation as previously reported.

Ninety percent (90%) of participants were found to have reduced sebum secretion which appeared to reduce acne formation by approximately eighty-five percent (85%) as a result.

These results came out of trial uses and a combination of user reporting and measurement of results for users of a trial formulation in a controlled study. Results may vary. However, the generally positive responses are expected to indicate a likelihood that many users of DERMAGRANT™ would experience some or all of these results to varying degrees depending on individual factors.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claim.

What is claimed is:

1. A nutritional composition comprising:
    a tablet comprising:
        an egg extract derived from fish collagen dipeptide in the amount of 10.0 g;
        an extract derived from *Zea mays* l. maize in the amount of 1.81 g; and
        an extract derived from *Rubus idaeus* in the amount of 0.10 g.

* * * * *